(12) United States Patent
Kunze et al.

(10) Patent No.: US 7,615,075 B2
(45) Date of Patent: Nov. 10, 2009

(54) PLASTIC IMPLANT IMPREGNATED WITH A DEGRADATION PROTECTOR

(75) Inventors: Achim Kunze, Hamburg (DE); Markus Wimmer, Chicago, IL (US)

(73) Assignee: Rush University Medical Center, Chicago, IL (US)

(*) Notice: Subject to any disclaimer, the term of this patent is extended or adjusted under 35 U.S.C. 154(b) by 132 days.

(21) Appl. No.: 11/555,453

(22) Filed: Nov. 1, 2006

(65) Prior Publication Data

US 2007/0213834 A1 Sep. 13, 2007

Related U.S. Application Data

(60) Provisional application No. 60/733,748, filed on Nov. 4, 2005.

(51) Int. Cl.
*A61F 2/02* (2006.01)
*C01F 17/00* (2006.01)

(52) U.S. Cl. .................... 623/11.11; 420/416; 423/263

(58) Field of Classification Search ........................ None
See application file for complete search history.

(56) References Cited

U.S. PATENT DOCUMENTS

| 5,684,564 | A | 11/1997 | North |
| 5,858,700 | A | 1/1999 | Ausich et al. |
| 6,169,217 | B1 | 1/2001 | Cheryan |
| 6,784,351 | B2 | 8/2004 | Hauptmann et al. |
| 2003/0012325 | A1* | 1/2003 | Kernert et al. ............... 376/202 |
| 2003/0208096 | A1* | 11/2003 | Tam et al. ...................... 600/3 |

OTHER PUBLICATIONS

RD 484072—Derwent abst, Aug. 2004, anonymous.*

* cited by examiner

*Primary Examiner*—Cecilia Tsang
*Assistant Examiner*—Christina Bradley
(74) *Attorney, Agent, or Firm*—Gerald T. Shekleton; Husch Blackwell Sanders Welsh & Katz

(57) ABSTRACT

A plastic implant device for a mammal that contains a rare earth metal compound tracer and a method for detecting degradation such as wear of the implanted device are disclosed. The tracer can also be present with a separate antioxidant or the tracer compound can be can be the salt of a $C_6$-$C_{22}$ unsaturated carboxylic acid. The rare earth metal compound tracer is released when the prosthetic is worn down or otherwise degraded in the mammalian body in which it was implanted. The presence and amount of released tracer present in a body fluid or tissue sample measured and is proportional to the degree of degradation of the implant.

24 Claims, 2 Drawing Sheets

PLASTIC IMPLANT IMPREGNATED WITH A DEGRADATION PROTECTOR

CROSS-REFERENCE TO RELATED APPLICATION

This application claims priority from Ser. No. 60/733,748 filed on Nov. 4, 2005, whose disclosures are incorporated by reference.

TECHNICAL FIELD

The present invention relates to a plastic implant that contains an implant degradation protector. Also disclosed is a method for detecting degradation such as wear of an implant in vivo, as well as an in vitro method for assaying wear of materials to be used in an implant.

BACKGROUND ART

There are approximately 200,000 hip replacement surgeries each year in the U.S. alone and about 800,000 worldwide. The number of knee replacement surgeries is approximately double this amount. In the future, the number of hip, shoulder, disk and knee replacement surgeries will continue to grow exponentially as the population ages.

Hip replacement surgery entails surgical intervention of two parts of the hip joint, the acetabulum (a cup-shaped bone in the pelvis) and the femoral head (the ball-shaped end of the thigh bone), then replacing each with smooth artificial surfaces. Shoulder replacements are similar, with knee and disk replacements being somewhat more complex. Exemplary artificial surfaces are high-density plastic, metal, and ceramic materials.

Hip replacements are used illustratively herein because they are most frequently carried out. Total hip replacements are most often performed for severe painful arthritic conditions but sometimes are performed for other problems such as deformities, fractures, tumors, or aseptic necrosis of the bone. In the majority of cases, hip replacement surgery is very successful in relieving pain, restoring function, and markedly improving the quality of life for patients with hip disease. The caveat is that the average life of a prosthetic implant is only about ten years. This relatively short functional existence is due to problems with decomposition (wear) of the prosthetic's fabrication materials and loosening of the joint due to osteolysis (bone loss) and other complications such as fatigue and degeneration of the artificial joint.

Wear debris and the resulting osteolysis from inflammatory cellular responses to wear debris are the most significant factors contributing to failure of hip replacements. Osteolysis, when undetected and untreated, can result in massive bone loss and implant failure.

Joint revision (replacement) procedures can be more difficult than the original surgery due to diseased, damaged, and decomposed bone in the area of the former prosthesis. Often there is little original natural bone remaining to attach a new prosthesis after the damaged prosthesis is removed. The magnitude of this problem is significant. For example, in 1996, total hip revision rates were about one third of the primary hip replacements. The function and long term survival of revision total hip arthroplasty is generally inferior to primary hip arthroplasty and leads to a worsened quality of life for many patients.

The amount of wear in a hip prosthesis is dependent upon many factors, including the materials used in fabrication, the weight of the patient, the age of the patient, and the patient's activity level, to name just a few. As mentioned above, materials commonly utilized in fabrication of hip prosthetics include plastic (ultra high molecular weight polyethylene, UHMWPE), metal (titanium or cobalt-chromium alloy), or alumina and zirconia ceramics.

The amount of wear for polymeric materials is in the region of 50-100 $mm^3$ per year for UHMWPE and 10 $mm^3$ (or smaller) per year for the newest cross-linked UHMWPE. The wear debris comes from the grinding of the metal against the polymer as the patient moves the prosthetic hip. Metal on metal and ceramic on ceramic implants sometimes have less wear debris than plastic implants; however they come with other risks, including suffering adverse biological effects to increased metal ions in the body, experiencing chipping of ceramic components, and risking fracture of the implant. Also, with metal and ceramic implants there are additional hurdles to overcome in fabrication such as the difficulty in obtaining conforming surfaces and consistently correct clearances. Lastly, wear debris from a prosthesis can also lead to bacterial infection in the bone causing failure of the prosthesis.

Current in vivo methods for measuring wear of a prosthetic implant are limited to radiological surveying and physical examination of the patient. However, in practice, both of these methods are truly useful only for detecting painful, catastrophic prosthetic failure, such that which happens in implant fracture or severe loosening from massive bone loss. Lesser amounts of implant decomposition are very difficult to diagnose due to the modest degree of physical symptoms.

In addition to wear, artificial joints, particularly those made of UHMWPE, a preferred artificial joint material, also degrade and fatigue due to free radical reactions that can occur prior to implantation and also in vivo, during use. Free radicals are typically generated prior to implantation by gamma irradiation of the artificial joint during sterilization, even when the sterilization is carried out in the substantial absence of oxygen. Free radicals are also generated in vivo due to mechanical chain scission or chemically by the action of blood- or serum-borne oxidants.

As mentioned before, radiology often underestimates the amount of wear due to implant decomposition. In addition, the method is imprecise, and as such, is not reliable for diagnosing less than component failure and/or catastrophic loss of bone stock. The reason for this unreliability is the physical difficulty in measuring small incremental changes that the prosthetic components may have made by X-ray methods. It is also difficult to standardize radiographs. In addition, there are health risks such as cancer due to the patient repeatedly being X-rayed multiple times. Furthermore, in polyethylene prosthetics, fluid absorption and/or creep of the polyethylene samples can be in the same order of magnitude as the wear itself. For these reasons, evaluation of in vivo wear of prosthetic implants, especially knee replacements, has been most precisely diagnosed from surgically removed implants.

Thus, there is an urgent need for a process for early detection and quantification of prosthetic implant wear. It is desirable that such a process be accurate so as to address smaller changes in prosthetic wear reliably. It is also desirable that the process be safe for the patient. The invention described hereinafter not only provides such a process but a novel plastic prosthesis that contains a tracer to facilitate such a process.

BRIEF SUMMARY OF THE INVENTION

The present invention contemplates a plastic implant and a method of using that implant for determining the rate of implant degradation within a mammalian body. One aspect of the present invention contemplates a plastic implant such as a prosthesis that contains a rare earth metal compound, preferably a europium compound, such as a salt of a $C_1$-$C_{22}$ carboxylate as a tracer for the diagnosis of prosthetic implant wear.

A second aspect of the invention is a degradation protector/tracer for the in vivo protection of a plastic prosthetic implant and diagnosis of prosthetic implant wear. The degradation protector/tracer is a rare earth metal salt, preferably, a europium salt, of a $C_6$-$C_{22}$ unsaturated carboxylate such as europium 2- or 3-hexenoate, oleate, linolenate or gallate that is substantially homogeneously distributed throughout the synthetic plastic.

In another embodiment, a rare earth metal compound, preferably, a europium salt of a $C_1$-$C_{22}$ carboxylate such as europium acetate or stearate, is used as a tracer for degradation along with an antioxidant amount of an antioxidant that is soluble in the implant plastic such as alpha-tocopherol, ascorbic acid, butylated hydroxyanisole, butylated hydroxytoluene, or a carotenoid such as a carotene like β-carotene, lycopene, or a xanthophyll like zeaxanthin or lutein.

The synthetic plastic in each of the above embodiments is preferably ultra high molecular weight polyethylene or polyetheretherketon where the implant is intended to remain in the host body.

In yet another aspect, a method for detecting decomposition of a prosthesis implanted in a human patient is contemplated. The prosthesis comprises synthetic plastic containing a tracer amount such as about 0.0005 to about 2 weight percent of a rare earth metal salt tracer. Here, a fluid or tissue sample from the patient having the implanted prosthesis is provided and that fluid or tissue sample is analyzed for the presence and quantity of rare earth metal salt tracer. Here, the presence and quantity of the rare earth metal in the fluid or tissue sample is proportional to the degree of decomposition of the implanted prosthesis.

The present invention has several benefits and advantages.

One benefit is that the invention provides a novel prosthetic implant that contains a free radical degradation inhibitor that can prolong the useful lifetime of a prosthetic joint.

An added benefit of the invention is that a free radical degradation inhibitor/tracer combination can be present in the joint that can prolong the useful life of the joint and can be used to easily and accurately diagnose degradation of the prosthesis in a mammal.

Another benefit is that the assay is reliable and accurate for detecting small changes in prosthetic wear so as to avoid catastrophic failure and subsequent injury to the patient.

Yet another benefit is that this assay can be utilized for pre-clinical wear testing making costly, time consuming and error prone weight measurements unnecessary.

Still further benefits and advantages of the invention will be apparent to the worker of ordinary skill from the disclosure that follows.

BRIEF DESCRIPTION OF THE DRAWINGS

In the drawings forming a portion of this disclosure

Figure 1:
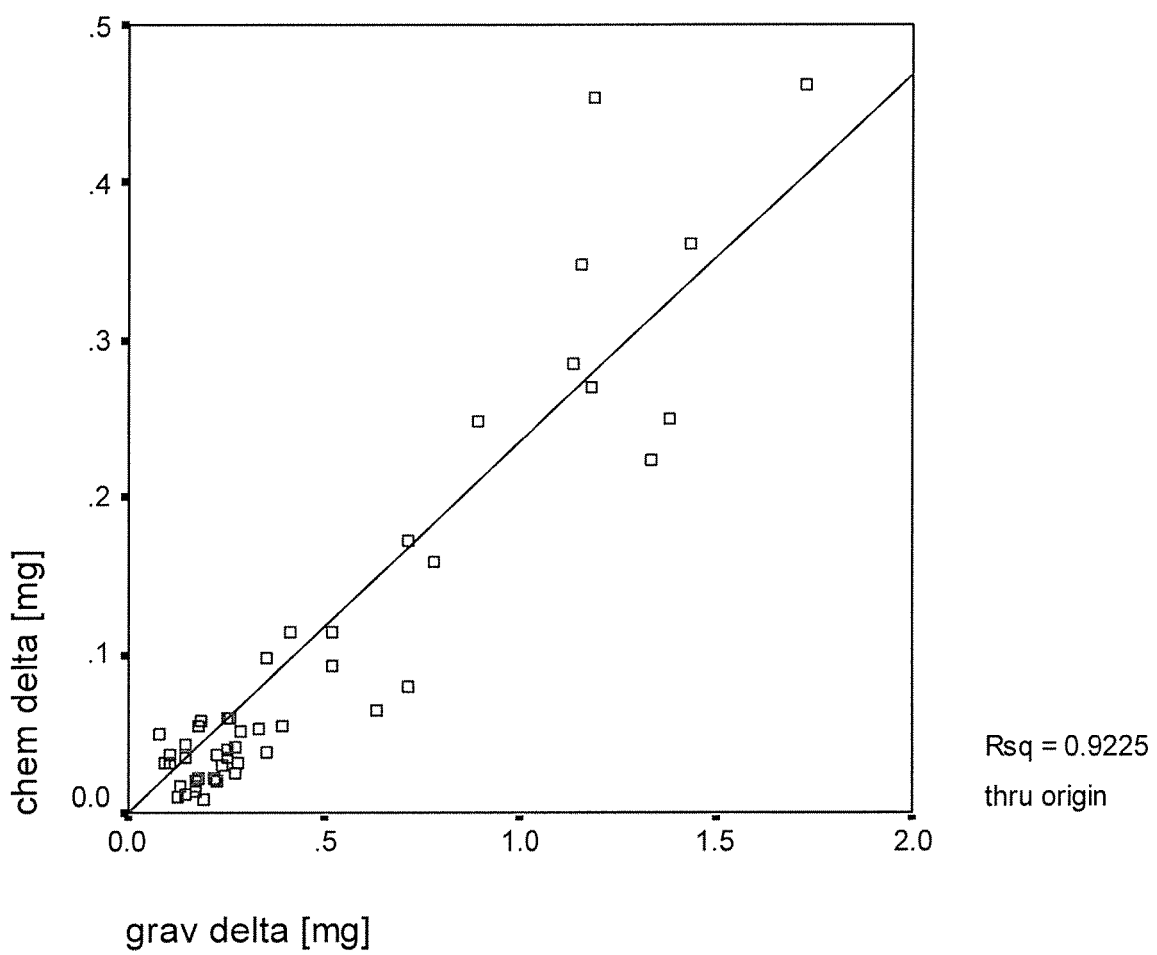
FIG. 1 shows a comparison between weight differences as determined from the discrete measurement points (abscissa-grav delta) and calculated polyethylene content in serum (ordinate-chem delta) based on the measured europium concentration. The correlation was highly significant (p<0.0001). Data were taken from six independent polyethylene samples at 8 discrete time intervals mechanically worn for 2 million cycles.
Figure 2:
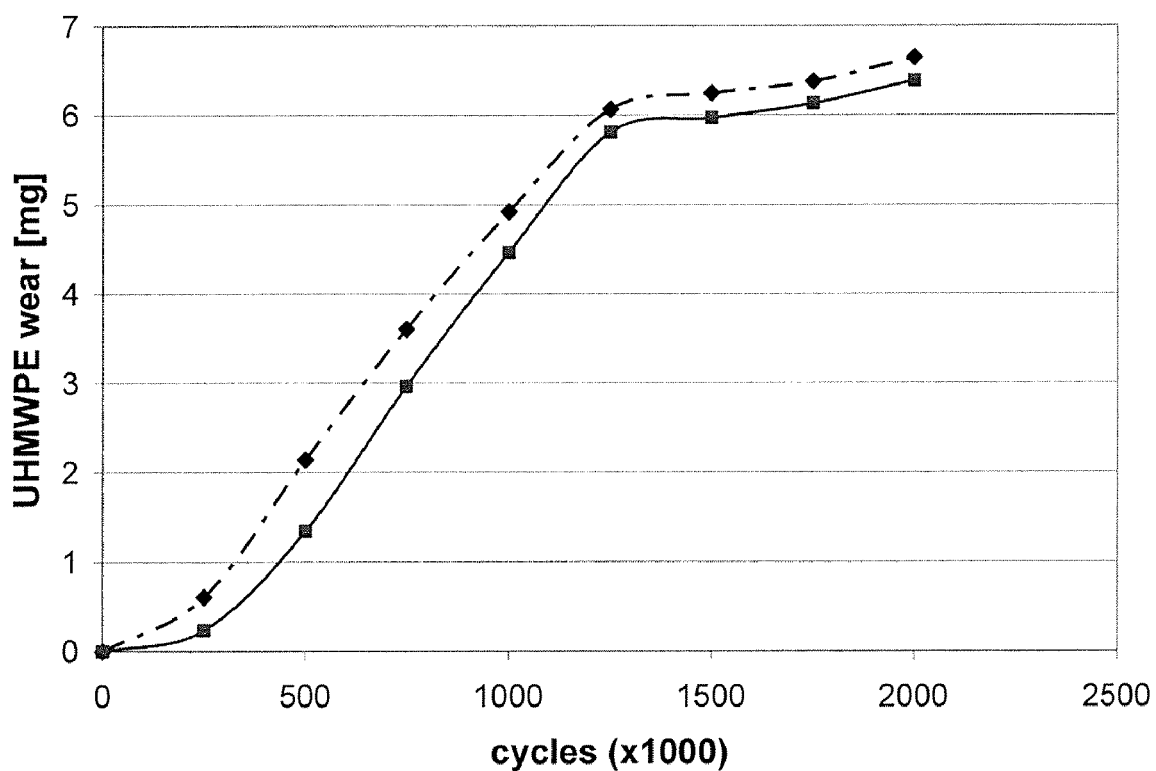
FIG. 2 shows a comparison between gravimetrically (dashed line and diamonds) and chemically (solid line and squares) determined wear rates (as above) of a single polyethylene sample.

Discrete measurement points were taken at every 250 k intervals. Note that the wear rate changes after 1,250 k cycles, a characteristic that is represented independently of measurement technique.

DETAILED DESCRIPTION OF THE INVENTION

Prosthetic implants can be made of metal, ceramic, plastic or a combination thereof. A synthetic plastic is utilized herein at least as a portion of a contemplated implant material in this invention. More preferably, a synthetic plastic of ultra high molecular weight polyethylene (UHMWPE) or polyetheretherketon is used to fabricate the prosthesis. In another embodiment, the plastic material, such as ultra high molecular weight polyethylene, is cross-linked to improve durability of the implant.

A plastic need only constitute a component of an implant, although entire implants can also be made of the plastic. This invention is concerned only with that plastic portion of an implant. As a consequence and for ease of understanding, the implant is discussed hereinafter as though it were entirely made of plastic. Any percentages or weights are to be understood to be based on the plastic portion of an implant where another material can also be present in the implant.

Substantially any joint can be fabricated as an implant or prosthesis, including maxillofacial, shoulder, elbow, ankle, finger, toe, wrist, or neck joint, rib, vertebra, and the like. However, a preferred prosthetic implant is either a hip joint or a knee joint or a spinal disk implant. A preferred tissue or fluid sample is a periprosthetic tissue biopsy or blood plasma, serum or urine.

The present invention contemplates a plastic implant impregnated with a tracer amount of a rare earth metal tracer compound for detecting degradation of the implant in the body of a mammalian host. The rare earth metal compound tracer is substantially homogeneously distributed throughout the synthetic plastic and is released as the implant such as a prosthesis is worn down or otherwise degraded in the mammalian body in which it had been implanted. The released rare earth metal tracer is detected in body fluids or tissue and its presence and amount are proportional to the degree of implant wear.

A rare earth metal compound has been chosen as a tracer because this type of metal is easily detected at very low levels in a laboratory and is normally not found in a mammalian body so that in most circumstances there will be no confusion as to the source of the tracer and the reason for its presence in a body fluid or tissue sample.

It is noteworthy that although almost any rare earth metal can be used as a component of the prosthetic tracer material, with the exception of the radioactive rare earth metal promethium, the rare earth metal europium is preferred in this instance. Another preferred rare earth metal is gadolinium. The term "rare earth" is used herein to include the lanthanide elements except promethium. Both europium and gadolinium compounds are utilized in human bodies and are generally non-toxic at the concentrations contemplated herein. The actinide rare earths are all radioactive and are not included herein.

In one preferred embodiment, the rare earth metal tracer compound in the implant such as a prosthesis is a rare earth metal salt. Preferably, the anion of that salt is a $C_1$-$C_{20}$ carboxylate, that is, the compound is a salt of a $C_1$-$C_{20}$ carboxylic acid. Illustrative $C_1$-$C_{20}$ carboxylic acids are well known in the art. More preferably, a salt such as either europium acetate or stearate is used as the tracer. Other well known salts such as chloride, nitrate and the like can also be utilized.

Rare earth compounds other than salts can also be used as a tracer. Illustrative compounds particularly include complexes of the rare earth metal cation with a complexing agent and one or more anions. One illustrative complex is formed from $Eu^{+3}$ nitrate and 9, 10-phenanthroline, another is gadopentetate dimeglumine. Such complexes are well known and studied and are readily obtained.

The amount of rare earth present in the prosthesis is a tracer amount. The tracer is preferably present in the prosthesis at about 0.0005 to about 2 percent by weight of the plastic. More preferably, the rare earth metal salt tracer is present in an amount of about 0.005 to about 1 percent by weight of the plastic. Most preferably, that amount is about 500 to about 1500 ppm or about 0.05 to about 0.15 weight percent. Each of these percentages is based on europium stearate, so that another material can be used proportionally.

A second aspect of the invention contemplates a degradation protector/tracer for the in vivo protection of a plastic prosthetic implant and diagnosis of prosthetic implant wear as discussed above. The degradation protector/tracer is a rare earth metal salt in which the cation is preferably, a europium salt, as discussed above. The anion of the salt here is a $C_6$-$C_{22}$ unsaturated carboxylate so that the salt is illustratively europium 2- or 3-hexenoate, oleate, linolate, linolenate or gallate that is substantially homogeneously distributed throughout the synthetic plastic. The anion is preferably a polyunsaturated carboxylate so that the degradation protector/tracer is the salt of a polyunsaturated carboxylic acid.

The preferred polyunsaturated fatty acids contain 18-22 carbon atoms and are the so-called "omega-6" fatty acids [e.g., the 18 carbon molecule, linoleic acid (18:2), that has two carbon-carbon unsaturated chemical bonds] and the so-called "omega-3" fatty acids, [e.g., the 18 carbon molecule, alpha-linolenic acid (18:3), that has three carbon-carbon unsaturated chemical bonds], as well as longer chain omega-3 molecules such as docosahexaenoic acid (DHA) and eicosapentaenoic acid (EPA) that have greater numbers of carbon-carbon unsaturated chemical bonds, and that are abundant in fish oils.

In yet another aspect of the invention, a rare earth metal tracer compound, preferably, a europium salt of a $C_1$-$C_{22}$ carboxylate such as europium acetate or stearate, is used as a tracer for degradation along with an antioxidant soluble in the plastic of the implant; i.e., the implant plastic, such as alpha-tocopherol, ascorbic acid, butylated hydroxyanisole, butylated hydroxytoluene, or a carotenoid such as a carotene like β-carotene, lycopene, or a xanthophyll like zeaxanthin, lutein, canthaxanthin or astaxanthin. The tracer is used in an amount discussed in the first embodiment, whereas the antioxidant is used in an anti-oxidant amount, as is known for such materials or is readily ascertainable using standard test methods.

Of the carotenoids, the carotene group that includes β-carotene and lycopene are hydrocarbons and are found as such in plants such as carrots and tomatoes. The xanthophyll group of carotenoids are mono- or di-alcohols and are usually found as fatty acid esters of those alcohols. Isolation of xanthophyll esters is described in U.S. Pat. No. 5,684,564 and U.S Pat. No. 6,784,351, whereas U.S. Pat. No. 6,169,217 teaches xanthophyll production from corn. U.S. Pat. No. 5,858,700 teaches isolation of lycopene from tomatoes. Several useful carotenoid compounds are available commercially, particularly the xanthophylls and xanthophyll esters.

Another aspect of the present invention utilizes the rare earth metal tracer in a bioresorbable plastic polymer of an implant as can be used for reconstructive and/or plastic surgery or for the slow release of a pharmaceutical product into the environment of the implant. Illustrative plastic polymers for this use include the polyhydroxy acids poly(lactic acid) (PLA), poly(glycolic acid) (PGA), poly(lactides-co-glycolides) (PLGA) poly(DL-lactide-e-caprolactone) and polyurethane polymers as are well known in the art and are available from Synthes, USA (West Chester, Pa.) and Polyganics (Groningen, Netherlands). Here, the rate of bioresorption of the plastic polymer can be ascertained by the rate of release of the rare earth metal tracer.

The tracer-containing implant that has been described thus far is preferably utilized with a method for detecting in vivo wear or other decomposition of such an implant in a mammal. This method of detecting the wear of a plastic implant as previously described herein is carried out ex vivo, and comprises the steps of providing a fluid or tissue sample from a mammal having the tracer-containing implant (device) and analyzing that fluid or tissue sample for the presence and quantity of the rare earth metal compound tracer. The tracer is preferably analyzed by ion-coupled plasma mass spectroscopy and its presence and quantity in the fluid or tissue sample is proportional to the degree of decomposition of the implant.

Although this method is useful for an implant such as a prosthesis that can be implanted in any mammal, such as in a mouse, rat, rabbit, cat, dog, sheep, bovine, or horse, the mammal is preferably a human patient. Preferably, the implanted prosthesis is a hip joint or a knee joint. The fluid or tissue sample is preferably (blood) plasma, serum, or urine or a periprosthetic biopsy.

An improved in vitro method for detecting decomposition of plastic or hybrid material present in a prosthesis tested in a wear simulator in which a liquid lubricant is used during testing comprises another aspect of this invention. Here, the improvement comprises substantially homogeneously dispersing a tracer amount of a rare earth salt in the plastic or hybrid material being tested in the wear simulator. The liquid lubricant is assayed at one or more times such as before, during and after wear test is completed for the presence and quantity of rare earth present. The presence and quantity of the rare earth in the liquid lubricant is proportional to the degree of decomposition of the tested plastic or hybrid material. This method is illustrated hereinafter.

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

EXAMPLE 1

Preparation of a Polyethylene Prosthesis Containing Europium Acetate Tracer

In this example, several small pins of ultra high molecular weight polyethylene (UHMWPE) containing europium acetate tracer were manufactured and their physical properties assayed. To begin, nascent ultra high molecular weight polyethylene powder was mixed with a solution of europium acetate as described in detail below. Different mixing techniques such as liquid nitrogen milling and n-hexane etching were tried to further homogenize the tracer before consolidation. Tracer homogenicity was analyzed by scanning electron microscopy and backward concentration measurement. The pins were then molded (10 mm diameter) and run on a 0.5×0.5 mm square motion pin-on-disk testing apparatus to test the effects of tracer addition on wear. The wear test was conducted in a lubricant that contained 30% bovine serum to simulate the proteins of an in vivo environment. Liquid samples were taken at regular intervals during the wear test. The presence of europium was analyzed in those samples and the UHMWPE wear was calculated and compared with the weight loss of the pins.

Preparing the Tracer

A solution of about 10 mg/ml europium was made by weighing about 1.0824 g europium acetate, $Eu(OOCCH_3)_3$, (Alfa Aeser) and dissolving it in 50 ml of deionized water >15 MΩ (Milli-Q™)

Stoichiometric data: europium acetate, $Eu(OOCCH_3)_3$: 328.96 g/mol, Eu: 151.96 g/mol.

Mixing the Tracer with UHMWPE

A. About 10 grams of nascent UHMWPE (PE) powder was weighed into a 50 ml round flask and 7 crystal balls of about 8 mm diameter each were added to it. About 20 ml of Eu-acetate solution above was mixed with the UHMWPE and homogenized by use of an ultrasonic bath for 5 minutes. The water then was evaporated on a rotary evaporator for about 20 minutes and the remaining water was removed by lyophilization and/or drying over phosphorus oxide ($P_2O_5$) in a desiccator. The dry powder tracer mixture was transferred to an agate ball mill, 80 mm diameter with 3-agate balls, 25 mm diameter each. Liquid nitrogen (40 ml) then was added to the mill, and the mill was run for 3 minutes. The theoretical concentration of the tracer (Eu) was 10 mg per ml.

B. Nascent PE powder is mixed with a solution of tracer alone, for example Eu-stearate. Here, the solution contains ligroin (boiling point range of 150-180° C.), n-hexane, cyclohexane or any other organic solvent capable of providing a good solubility for the tracer and a good miscibility with the polyethylene powder and sufficient tracer to provide a tracer concentration of about 50 ppm to about 3000 ppm. The solvent is separated from the nascent PE powder by means of rotary evaporation, the resulting material is assayed for homogeneity with ICP-MS.

C. Nascent PE powder is mixed with a solution of tracer and lycopene. The solution comprises ligroin, n-hexane, cyclohexane or any other organic solvent capable of providing a good solubility for the tracer, e.g. Eu-stearate, and the lycopene a good miscibility with the polyethylene powder. The tracer concentration is illustratively 50 ppm, whereas the lycopene concentration can be about 50 ppm to about 3000 ppm. The solvent is separated by means of rotary evaporation, and the resulting material is assayed for homogeneity with HPLC and ICP-MS.

Analyzing the Tracer Homogeneity

Tracer homogeneity was then assayed by scanning electron microscopy as well as by backward concentration measurements. Different masses of Tracer-UHMWPE-powder (T-powder) were used to study the homogeneity of the tracer. A Perkin-Elmer MULTIWAVE™ microwave digestion system with a 6-position rotor and 50 ml Quartz glass vessels was used. Samples of about 1, 4, 7, 10 and 100 mg of T-powder were weighed into quartz containers. The microwave digestion was done by means of nitric acid. About 1 ml of deionized water (>15 MΩ) and about 2 ml of $HNO_3$ (sub-boiling distilled, suprapure grade) were added to the T-powder and the digestion was carried out as described in Table 1, hereinafter. Six replicates for each mass of T-powder were analyzed.

Table A, below, provides data for the variance of findings for the 4 mg weight in parts per thousand.

TABLE A

| Sample | T-Powder (mg) | Eu/1000 |
|---|---|---|
| S1 | 4.9 | 14.2 |
| S2 | 4.8 | 13.5 |
| S3 | 4.8 | 13.5 |
| S4 | 4.9 | 13.6 |
| S5 | 4.6 | 13.6 |
| S6 | 4.7 | 13.3 |
| Mean | | 13.6 |
| Standard Deviation | | 0.306050 |
| RSD in % | | 2.2 |

Measurement of europium concentration follows the procedure as described below for serum samples during wear test.

Wear Test

A wear simulator was used to assay the effect of the tracer addition on the wear properties of the UHMWPE. Two dimensional interface motion is generated by axial oscillation of two opposing pins and a hip ball. A contact load of 1000N is generated using a pneumatic pressure control device. Testing is carried out in a protein containing lubricant at 37° C. Two test groups (marked and non-marked UHMWPE) comprised of six pins each are analyzed over 2 million cycles per articulation. Serum samples are taken at ten defined intervals (including 250, 500, . . . , to $2×10^6$ cycles). These samples are tested for the presence of the rare earth tracer via ICP-MS. Additionally, for both groups, changes in mass are determined every 500,000 cycles and corrected using a soak control.

Procedure

At the above-specified time intervals, 2 ml of the lubricant were pipetted into a single polypropylene (PP) sample tube. The sample was taken by use of a 2 ml PP syringe. The samples were transported into the laboratory and thoroughly mixed by ultrasound prior to digestion. One ml of serum was pipetted into the Microwave container. The pipettes used were EPPENDORF™. Two ml of $HNO_3$ was added to the serum. The containers were shut and embedded into the microwave 6-vessel rotor with a 6-vessel capacity. The rotor was placed into the microwave oven for driving the temperature/time program as listed below (Table 1).

TABLE 1

Microwave Sample Preparation System
PERKIN-ELMER MULTIWAVE ®

| Phase | Power (W) | Time (mm:ss) | Power (W) | Fan |
|---|---|---|---|---|
| 1 | 100 | 5:00 | 500 | 1 |
| 2 | 500 | 15:00 | 800 | 1 |
| 3 | 0 | 15:00 | 0 | 3 |

Parameter for quartz glass vessels, 50 ml, operating pressure up to 74 bar (7400 kPa), solution reaches a temperature of 190° C. during digestion process.

After cooling to room temperature, the containers were opened under a HERAEUS™ clean bench with filter capable for providing clean air. The clear solution was transferred into a 20 ml glass flask and deionized water was added. Prior to measurement, the samples were diluted with $H_2O$ Millipore and adjusted to contain 2 µg/l Rh as an internal standard. A simultaneous measurement of europium isotopes 151 (isotopic abundance: 47.8%) and 153 (isotopic abundance: 52.2%) was made using a quadrupole inductively-coupled plasma mass spectrometer (ICP-MS). As both isotopes give nearly the same readings, Eu 153 was used for calculation. A Perkin-Elmer SCIEX ELAN® 6000 quadrupole ICP-MS was used, equipped with an AS-91 Auto sampler. Conditions for the determination of europium, see Table 2.

TABLE 2

| ICP-MS conditions for the measurement of Eu | |
|---|---|
| Isotopes, Eu | 151, 153 m/z |
| Internal Standard, Rh | 103 m/z |
| Standard stock solutions | Eu, Rh: 1000 mg/l |
| $H_2O$ Millipore | Milli-Q ™ |
| $HNO_3$ (65%) | sub boiling distillation grade, lab made |
| Calibration | 0/0.1/0.5/1/2/5/10 µg/l Eu |
| Linearity of the curve Eu 153 m/z | 0.999973 |
| ICP RF power | 1100 W |
| Argon gas flow | 15 l/min |

The presented method was capable in quantifying wear of polyethylene (UHMWPE) accurately in extremely low masses of wear debris. As a first approach Eu-acetate has been applied as tracer substance. Homogeneity of the water-soluble tracer and its ability to be mixed with UHMWPE-powder are to be considered satisfactory. The influence of the mixing technique is demonstrated and showed absorbent effects of the tracer with the glassware used for the process of staining. Nevertheless, scanning electron microscopy (SEM) and ICP-MS measurements demonstrate the availability of a homogeneous tracer-UHMWPE, with a concentration range of europium from 13.6±0.3 per mill. The milling process using liquid nitrogen was shown to be as effective as the partial dissolving of the UHMWPE-powder with n-hexane as organic solvent for polyethylene.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. An implant for a mammal that comprises a plastic that contains a tracer amount of a europium $C_1$-$C_{22}$ carboxylate substantially homogeneously distributed throughout the plastic.

2. The implant according to claim 1 wherein the europium $C_1$-$C_{22}$ carboxylate tracer is present in an amount of about 0.0005 to about 2 percent by weight of the plastic.

3. An implant for a mammal comprising plastic that contains about 0.0005 to about 2 percent by weight of europium $C_1$-$C_{22}$ carboxylate tracer substantially homogeneously distributed through out the plastic.

4. The implant according to claim 3 wherein the europium $C_1$-$C_{22}$ carboxylate is a europium $C_6$-$C_{22}$ unsaturated carboxylate.

5. The implant according to claim 3 that additionally contains an antioxidant amount of an antioxidant soluble in the implant plastic.

6. The implant according to claim 3 wherein the europium $C_1$-$C_{22}$ carboxylate tracer is present in an amount of about 0.005 to about 1 percent by weight of the plastic.

7. The implant according to claim 3 wherein said plastic is ultra high molecular weight polyethylene or polyetheretherketon.

8. The implant according to claim 3 wherein said plastic is a bioresorbable implant.

9. The implant according to claim 8 wherein said plastic contains a pharmaceutical product which is released into its environment.

10. A prosthesis for implantation in a mammal comprising a plastic that is ultra high molecular weight polyethylene or polyetheretherketon that contains about 0.005 to about 1 weight percent of a europium $C_1$-$C_{22}$ carboxylate tracer substantially homogeneously distributed through out the synthetic plastic.

11. The prosthesis according to claim 10 wherein the europium $C_1$-$C_{22}$ carboxylate is europium acetate or europium stearate.

12. The prosthesis according to claim 10 wherein the europium $C_1$-$C_{22}$ carboxylate is a europium $C_6$-$C_{22}$ unsaturated carboxylate.

13. The prosthesis according to claim 10 that additionally contains an antioxidant amount of an antioxidant soluble in the implant plastic.

14. The prosthesis according to claim 10 wherein the ultra high molecular weight polyethylene is cross-linked.

15. The prosthesis according to claim 10 that is a hip joint.

16. The prosthesis according to claim 10 that is a knee joint.

17. The prosthesis according to claim 10 that is a spinal disk implant.

18. A method for detecting decomposition of an implant in a mammal, which implant comprises plastic impregnated with a tracer amount of a europium $C_1$-$C_{22}$ carboxylate, said method comprising the steps of:
   (a) providing a fluid or tissue sample from the mammal having the implant; and
   (b) analyzing that fluid or tissue sample for the presence and quantity of the europium $C_1$-$C_{22}$ carboxylate tracer, wherein the presence and quantity of the europium $C_1$-$C_{22}$ carboxylate tracer in the fluid or tissue sample is proportional to the degree of decomposition of the implant.

19. The method according to claim 18 wherein the europium $C_1$-$C_{22}$ carboxylate tracer is present in an amount of about 0.0005 to about 2 percent by weight of the plastic of the implant.

20. The method according to claim 18 wherein said mammal is a human patient.

21. The method according to claim 18 wherein said implant is a prosthesis.

22. The method according to claim 18 wherein the europium $C_1$-$C_{22}$ carboxylate is a europium $C_6$-$C_{22}$ unsaturated carboxylate.

23. The method according to claim 18, wherein the implant additionally contains an antioxidant amount of an antioxidant soluble in the implant plastic.

24. The method according to claim 18 wherein said plastic is ultra high molecular weight polyethylene or polyetheretherketon.

* * * * *